(12) United States Patent
Stuettler et al.

(10) Patent No.: US 8,456,739 B2
(45) Date of Patent: Jun. 4, 2013

(54) MICROSCOPE HAVING A MICROSCOPE BODY AND A STAND FORMED BY A PLURALITY OF COMPONENTS TO PROVIDE A SUPPORTING FUNCTION OR TO ENABLE POSITIONING OF THE MICROSCOPE IN THE ROOM

(75) Inventors: Herbert Stuettler, Au (CH); Christophe Apothéloz, Gockhausen (CH); Andreas Tedde, Hinterforst (CH); Urban Wenk, Diepoldsau (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 325 days.

(21) Appl. No.: 12/837,528

(22) Filed: Jul. 16, 2010

(65) Prior Publication Data

US 2011/0019271 A1 Jan. 27, 2011

(30) Foreign Application Priority Data

Jul. 23, 2009 (DE) .......................... 10 2009 034 309
Jun. 25, 2010 (DE) .......................... 10 2010 025 114

(51) Int. Cl.
*G02B 21/06* (2006.01)
*G02B 21/00* (2006.01)

(52) U.S. Cl.
USPC ............................ 359/390; 359/368; 359/385

(58) Field of Classification Search
USPC .................................. 359/368–390, 800–819
See application file for complete search history.

(56) References Cited

U.S. PATENT DOCUMENTS

| 2,766,655 | A |   | 10/1956 | Pinkowski |
| 3,240,925 | A | * | 3/1966  | Paschke et al. ................. 362/33 |
| 5,048,941 | A | * | 9/1991  | Hamada et al. ............... 359/368 |
| 5,250,966 | A | * | 10/1993 | Oda et al. ...................... 351/208 |
| 5,748,366 | A | * | 5/1998  | Yasunaga et al. ............. 359/368 |
| 6,543,914 | B2 | * | 4/2003 | Sander .......................... 362/401 |
| 2004/0263960 | A1 | * | 12/2004 | Obuchi ....................... 359/385 |
| 2007/0030564 | A1 |   | 2/2007  | Bertschi et al. |
| 2007/0228262 | A1 | * | 10/2007 | Cantin et al. ................. 250/221 |
| 2009/0109526 | A1 |   | 4/2009  | Sander |

* cited by examiner

*Primary Examiner* — Thong Nguyen
(74) *Attorney, Agent, or Firm* — Hodgson Russ LLP

(57) ABSTRACT

The present invention relates to a microscope (1), preferably a dental microscope, including a microscope body (15) and a stand (2) formed by a plurality of components to provide a supporting function or to enable positioning of the microscope (1) in the room (11), the microscope body (15) and the stand (2) having cavities (16) therein. It is a feature of the present invention that at least one cavity (16) of the microscope body (15) and/or the stand (2) has a light source (17) provided therein whose light (17*a*, 17*b*, 17*c*) can pass outwardly through passage openings (18, 24, 27).

28 Claims, 14 Drawing Sheets

(Section VIII-VIII from Fig.6)

(Section IX-IX from Fig.1)

MICROSCOPE HAVING A MICROSCOPE BODY AND A STAND FORMED BY A PLURALITY OF COMPONENTS TO PROVIDE A SUPPORTING FUNCTION OR TO ENABLE POSITIONING OF THE MICROSCOPE IN THE ROOM

CROSS REFERENCE TO RELATED APPLICATIONS

This application claims priority of German patent application number 10 2009 034 309.1 filed Jul. 23, 2009, the entire disclosure of which is incorporated by reference herein. This application also claims priority of German patent application number 10 2010 025 114.3 filed Jun. 25, 2010, the entire disclosure of which is incorporated by reference herein.

FIELD OF THE INVENTION

The present invention relates to a microscope including a microscope body and a stand formed by one or more components to provide a supporting function or to enable positioning of the microscope in the room. These components are hereinafter jointly referred to as a stand. The stand includes one or more support arms, for example, in the form of a parallelogram linkage support.

BACKGROUND ART

Many different techniques are known for illuminating objects to be observed using a wide variety of different microscopes. Moreover, in particular for surgical stereomicroscopes, various techniques are known whereby additional information, such as, for example, information on the various operating conditions, or operating mode indications of the microscope, can be projected into one or more observation beam paths of such a microscope.

Thus, conventional microscopes typically have a light source for illuminating the object field to be viewed. The design and operation of the microscope and/or its stand are of minor importance in this connection. Also, to date, the microscope has not been used as a light source for the room in which it is located, and information on the microscope could only been read from a display or from discrete control elements, indicators, or the like.

Document DE102005036230B3 describes a microscope having light-emitting diodes mounted in the body or stand thereof to illuminate the object field.

Accordingly, the light-emitting diodes are used for purposes of object field illumination.

Document DE102007051909A1 discloses a microscope having a light source provided in the body thereof, said light source illuminating the object field via a deflection mirror. Thus, this light source is also used for purposes of object field illumination and does not have any other function.

Document U.S. Pat. No. 2,766,655A1 describes a phase contrast microscope whose object field illumination means is arranged within the stand, from where illumination light is directed into the microscope body, and from there via a mirror onto the object field. Here, too, the illumination system is used exclusively for purposes of object field illumination.

SUMMARY OF THE INVENTION

It is, therefore, an object of the present invention to provide a microscope having an improved device, using the existing housings of the microscope and/or its stand.

More specifically, it is an object of the present invention to use the microscope and/or its stand more universally and, by implementing at least one additional light source besides a light source that may be provided for object field illumination, to enable the microscope and/or its stand to be used also for room illumination purposes or to illuminate the microscope or its stand (apart from the area to be viewed through the microscope) and, optionally, to make light available for further information purposes.

The present invention includes at least one light source which is disposed within the microscope body and/or the stand and which emits its light outwardly into the room through passage openings when in the operating condition, independently of the microscope illumination, and which is not used for purposes of object field illumination.

The light source and the passage openings may be designed to merely improve the perception of the microscope or the stand in space (for example, in twilight conditions).

More specifically, the light source and the passage openings may be designed to simulate different appearances of the microscope or stand using different light intensities or colors.

Yet more specifically, the light source and the passage openings may be designed to provide illumination effects which vary over time so as to distract the patient, and thus to increase the safety of the treatment.

Variation of the light color can best be accomplished by inserting color filters, or by using colored light-emitting diodes which are driven as needed and according to the desired color mixture.

The light source and the passage openings may also be designed to provide indirect room illumination.

In addition, the light source and the passage openings may be designed to deliver signals to a user and/or to change the visible exterior appearance of the microscope or stand using different light colors.

This illumination system for indirect external illumination may also include a plurality of light sources and a plurality of passage openings for the passage of this light into the room external to the microscope or stand.

To date, no techniques or devices are known which, except for external indicator lamps, such as externally mounted LEDs, would allow the appearance of the microscope or stand to be changed, or different operating conditions or operating mode indications to be displayed, on the exterior of the microscope body or stand and/or which would provide means for providing indirect room illumination.

However, it appears desirable to provide such additional display options so as to allow selected operating conditions of a microscope, or changes thereto, to be made visible not only to the operator, but also to other people, especially for example a patient, who are present in the room in which the microscope is located, and to do so independently of the image acquired by the microscope; i.e., the image of an object being viewed.

The present invention achieves the object described above, making it possible to implement both indirect room illumination and a means for distracting patients, and allowing operating conditions or operating mode indications, and also the extent of the microscope or its stand, to be displayed or made visible externally in a simple manner. In accordance with the present invention, at least one cavity of the microscope and/or the stand has/have a light source disposed therein whose light can pass outwardly into the room through one or more passage openings.

It is preferred for the light source to be variable, particularly preferably to be variable over time.

The passage openings are preferably disposed and configured such that the emerging light indirectly illuminates the exterior of the microscope or its stand, or the room in which it is located.

It is also preferred that the color and/or intensity of the light be adjustable and/or selectable.

The microscope is preferably a surgical microscope or a dental microscope.

The light sources preferably used for the indirect external illumination include inorganic light-emitting diodes (LED), organic light-emitting films (OLED), or what is known as "nanotubes". It is also possible to use laser diodes, which may be advantageous because of the spectrum and orientation of their radiation.

It is preferred that the light color of the one or more light sources used for the external illumination also be variable and/or freely selectable. This is preferably done in an automatically controlled manner. Thus, it is possible, for example, to drive a plurality of different color LEDs alternatively or together to produce specific light colors.

Preferably, a specific light color and/or light intensity, or the change thereof, is assigned to a specific operating condition of the microscope, or its further above-mentioned mechanical components, and to changes in such an operating condition. Such operating conditions or operating mode indications to be displayed, and their respective changes, may refer, for example, to a magnification setting of the microscope, diopter settings of eyepieces of the microscope, the balancing of a stand of the microscope, the operational readiness of accessories, such as a camera, the making of a video recording, the remaining service life of illumination devices for object illumination, etc.

Among a group of different operating conditions or operating mode indications to be displayed, particular preference is given to the following options:
- the light color is used to indicate a magnification setting of the microscope;
- the light color is used to indicate the operating condition of a zoom system or the diopter setting of an eyepiece of the microscope;
- in the common case of a microscope having two eyepieces which are individually adjustable to different diopter settings, it is preferred that different light colors be producible on two different exterior sides of the microscope body or the stand.

Particularly advantageous embodiments of the present invention are those in which a plurality of operating conditions or operating mode indications of the microscope can be displayed simultaneously by one or more different light colors.

It is also advantageous if at least one sensor is provided which measures the color temperature and/or the light intensity of an external room lighting and adapts the color and/or intensity of the light from the light source accordingly via an electronic control system (e.g., chameleon function).

It may also be advantageous if the light colors produced by the illumination system for the external illumination are complementary to, for example, the color of an external room lighting.

Preferably, the microscope according to the present invention has an aesthetically appealing and compact design, which advantageously minimizes space requirements. This appearance may be further enhanced by the choice of light.

Further embodiments of the present invention and variants thereof will become apparent from the dependent claims and the Figures.

The list of reference numerals is part of the disclosure.

The present invention is schematically described in more detail by way of example and with reference to Figures.

BRIEF DESCRIPTION OF THE DRAWING VIEWS

The Figures are described collectively. Identical reference numerals denote identical components; reference numerals having different indices indicate functionally identical or similar components. In the drawing, FIG. 1 is a view showing the arrangement of a first exemplary embodiment of a dental microscope which is mounted on a stand in such a way that it can be adjusted in three degrees of freedom, said stand including a base provided with rollers and a vertical pole on which there are arranged three support arms, the dental microscope being mounted on the third support arm, and the entire arrangement being located in a room which can be illuminated;

DETAILED DESCRIPTION OF EXEMPLARY EMBODIMENTS

Figure 1:
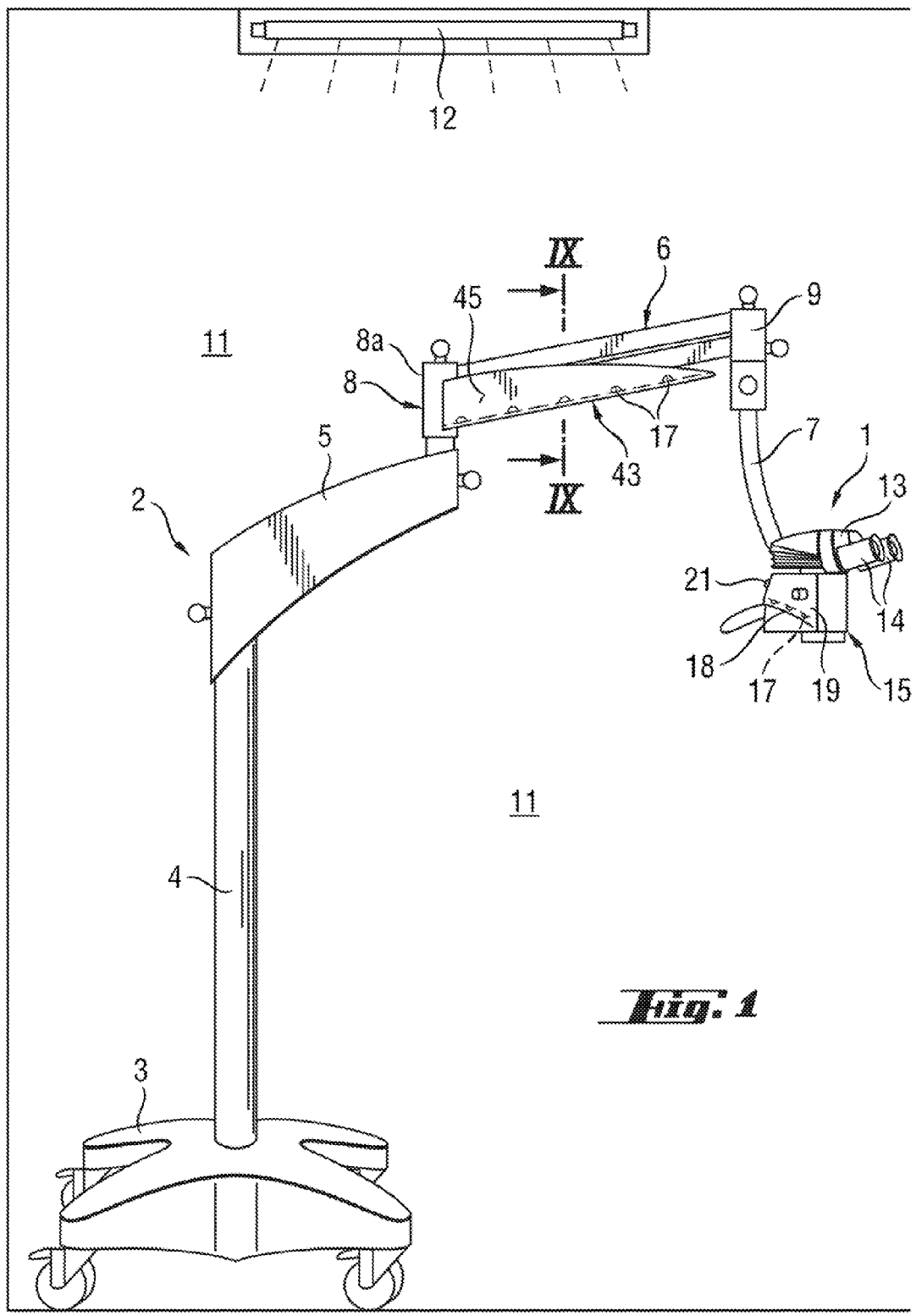

Referring to FIG. 1, a dental microscope 1 is mounted on a stand 2 in such a way that it can be adjusted in three degrees of freedom. Stand 2 includes a rolling base 3, a pole 4, a first support arm 5, a second support arm 6, and a third support arm 7. Support arms 5, 6, 7 are linked together by joints 8 and 9.

The entire arrangement is set up in a room 11 which is used as a treatment room and provided with what is referred to as external room lighting 12. Dental microscope 1 includes a head portion 13 which carries an eyepiece 14 and is mounted on microscope body 15.

Figure 2:
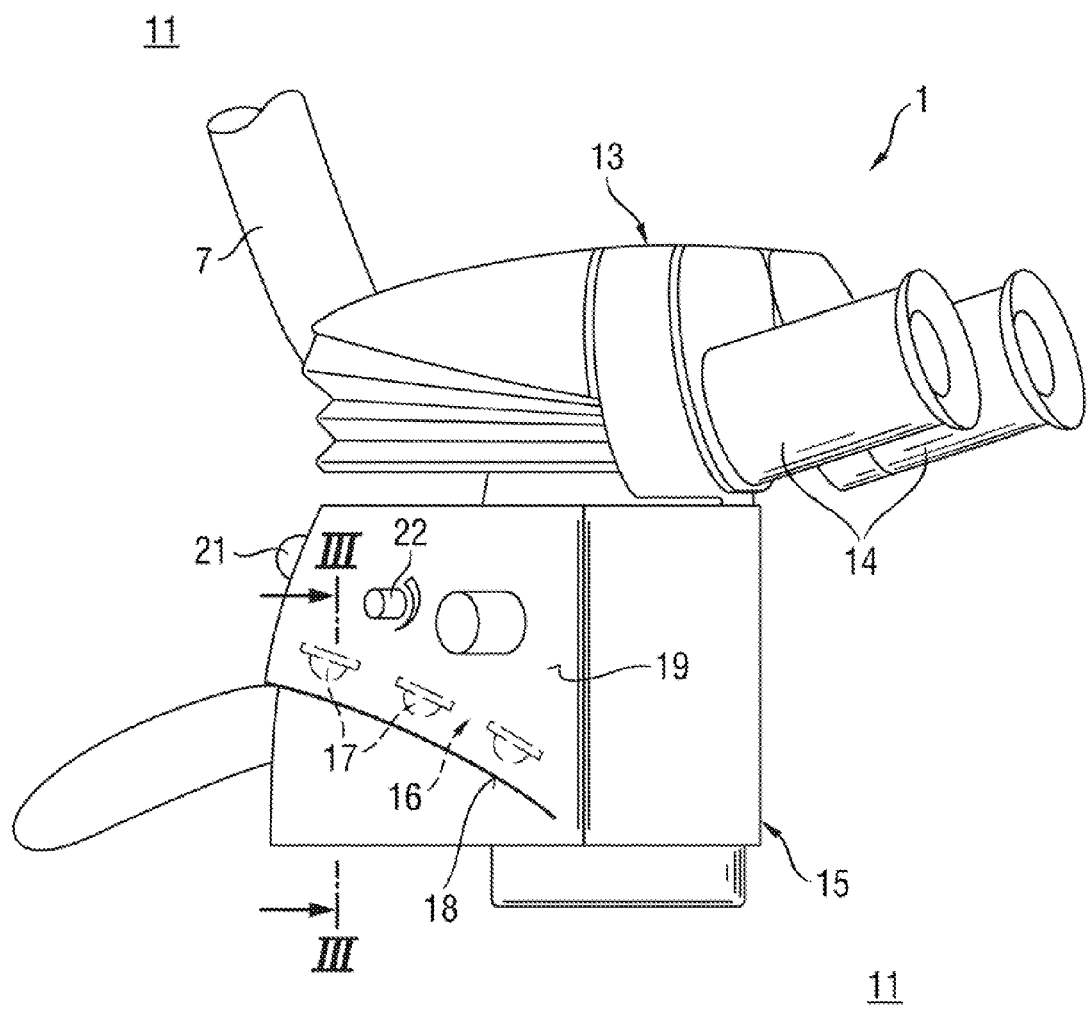
FIG. 2 is an enlarged view of the dental microscope shown in FIG. 1.
Figure 3:
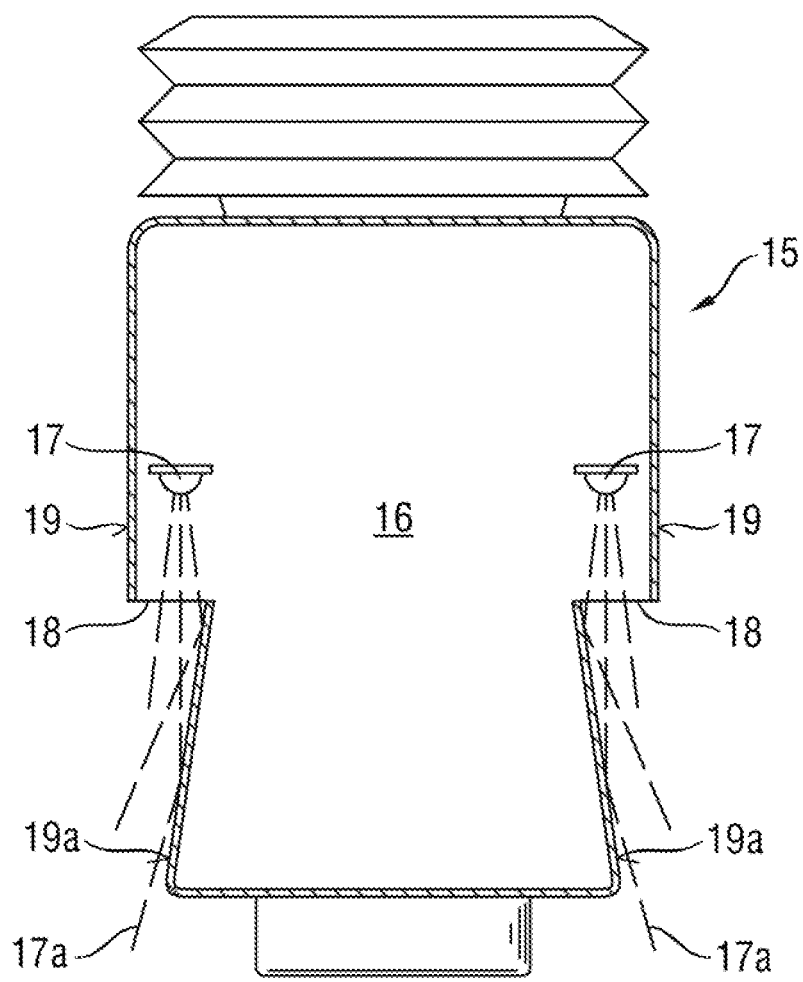
FIG. 3 is a vertical sectional view of the housing body of the dental microscope, taken in the plane of line III-III in FIG. 2 and showing an open light exit opening on each of the two sides.

As is shown particularly in FIGS. 2 and 3, light sources 17, which may be in the form of three LEDs, are arranged in cavity 16 of microscope body 15, the rays of light from said light sources emerging from the walls in a more or less downward direction through passage openings 18 formed in the sides and being partly reflected at inclined wall sections 19a. As a result, both the side walls 19 of microscope body 15 and their surroundings in room 11 are discreetly illuminated, which positively influences the appearance of microscope 1 and affects the treatment environment and the position of the microscope in an ergonomically favorable manner, even in a semi-darkened room 11.

Figure 14:
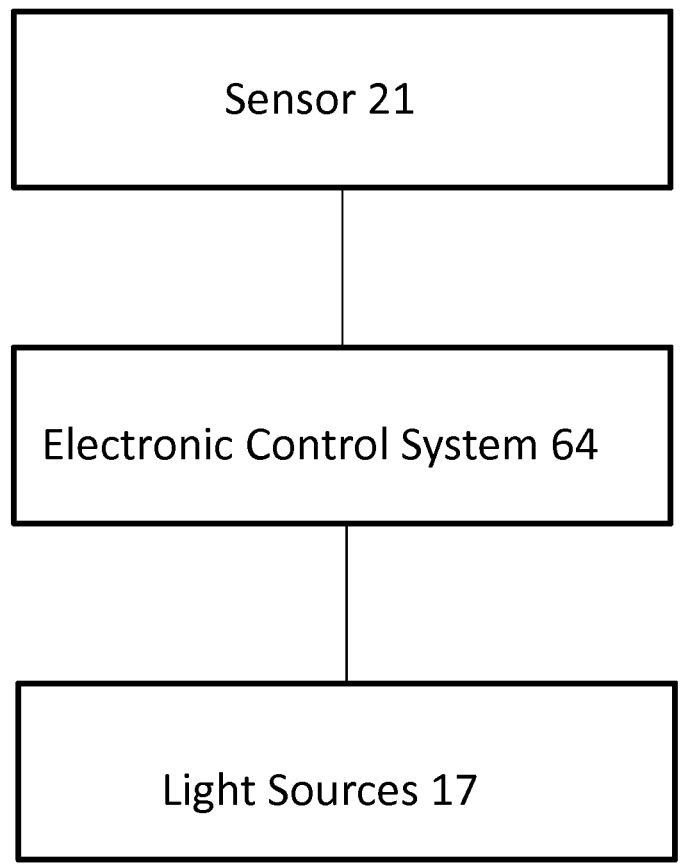
FIG. 14 is a schematic of an embodiment of the present invention showing an electronic control system connected to a sensor and associated with light sources.

A sensor 21 mounted on microscope body 15 measures the light intensity provided in room 11 by external room lighting 12 and is capable of controlling the color and intensity of the light from light source 17 via an electronic control system 64 according to corresponding, predetermined parameters (FIG. 14).

The balancing of the stand or microscope, or of other mechanical components or accessories of the microscope, may be accomplished using, for example, force sensors or torque sensors and may be associated with an electronic control system, which is also used to drive the light source(s) for the external illumination.

The remaining service life of light sources used in a microscope for object illumination may be determined, for example, from a table value read into the electronic control system of the external illumination system, for example, in accordance with a decay curve in tabular form, or based on an intensity value that is actually measured by a light-sensitive sensor and compared with stored reference values.

The operational readiness of electronic microscope accessories, such as a camera, may be deduced, for example, from an electronic feedback signal provided by such an accessory to the electronic control system. Therefore, the illumination system is advantageously associated with a microprocessor- or computer-controlled electronic control system.

The light intensity of light sources 17 can also be controlled manually, for example, using a rotary knob 22 on microscope body 15.

As is shown particularly in FIG. 3, light rays 17a from light sources 17 emerge downwardly here and are reflected into room 11 by an the inclined section 19a of wall 19, so that they illuminate both microscope body 15 and room 11.

Figure 4:
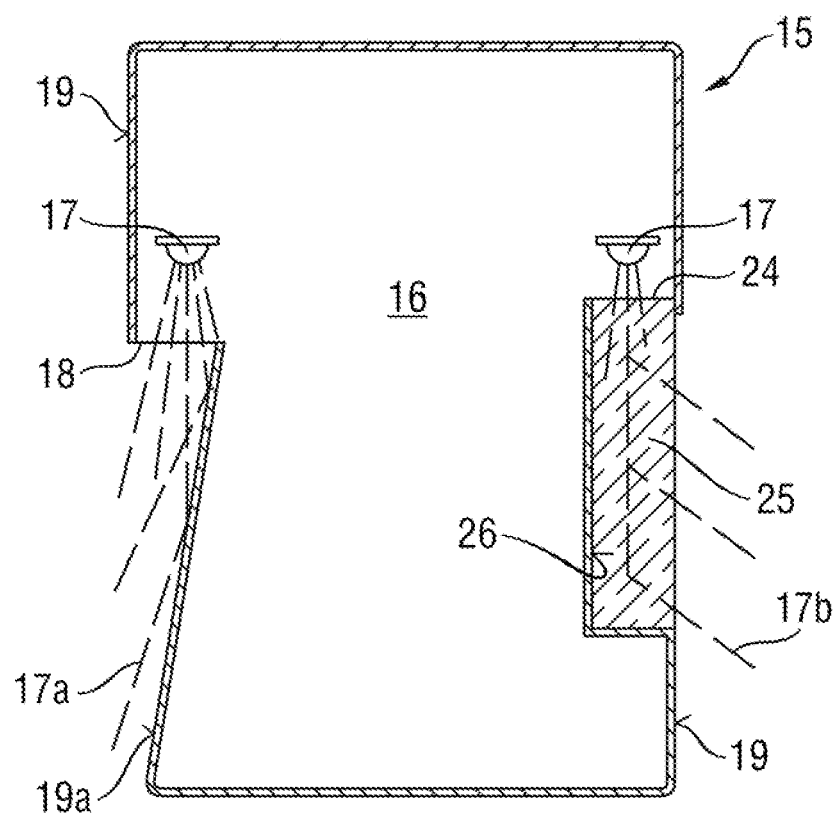
FIG. 4 is a vertical sectional view of the housing body similar to that of FIG. 3, but showing an open light exit opening on the left side and a different light exit opening on the right side, the latter being closed dust-tight with a transparent plate as a light-diffusing body.

FIG. 4 shows two variants of light passage openings. The left side shows the variant of FIG. 3, which features an open, slotted opening. This embodiment is suitable, for example, for illuminating room 11 away from the practitioner, making it possible to increase the brightness of the background to maximum levels. Light exit opening 24 shown on the right side is closed dust-tight with a transparent ground glass plate 25 which has light-diffusing properties and is inserted in a pocket or recess 26 flush with the exterior of wall 19. In this manner, wall 19 of microscope body 15 turns into a large-area luminous element which illuminates room 11 with diffuse, homogenized light, preferably toward the side of the practitioner. Alternatively, it is possible to equip both walls 19; i.e., the one on the left and the one on the right in FIG. 4, with a ground glass plate 25 as a luminous element having light-diffusing properties.

Figure 5:
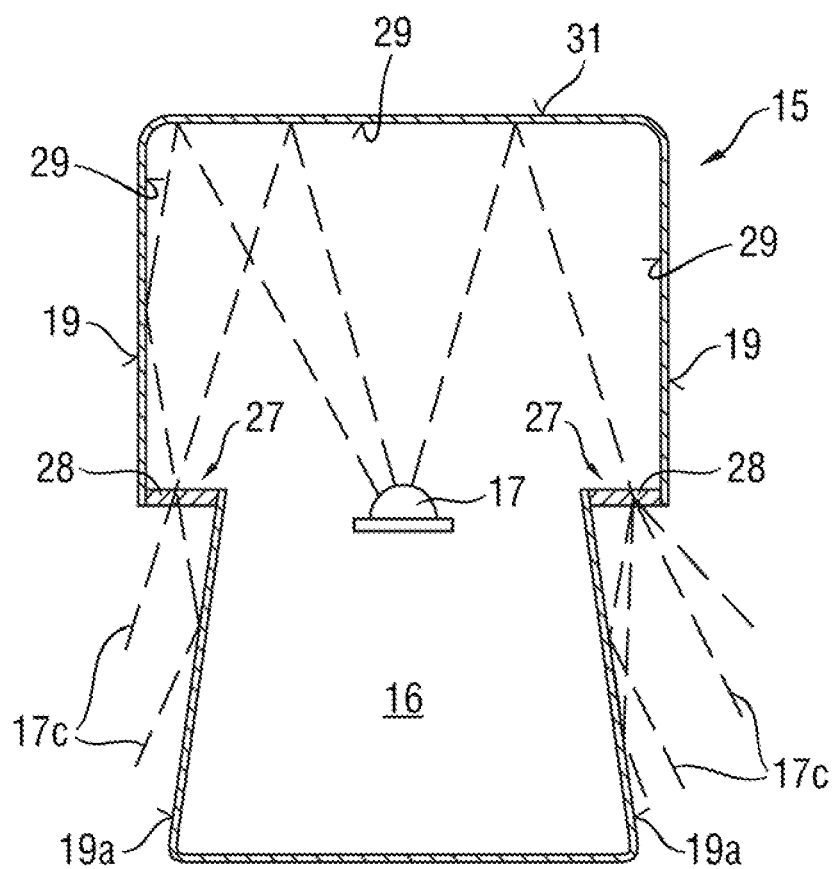
FIG. 5 is a vertical sectional view of the housing body similar to those of FIGS. 3 and 4, but showing the two light passage openings covered with diffusing glass plates.

FIG. 5 shows an embodiment in which light passage openings 27 are closed dust-tight with cover plates 28. These cover plates may have diffusing properties, and may thus be capable of diverging the light rays into sets of rays 17c. A portion of rays 17c may enter room 11 directly, while another portion is initially reflected at inclined wall sections 19a.

Preferably, at least one passage opening (optical passage) has a surface configuration which prevents light from being emitted directly into the room and produces diffuse light emission. This may be achieved, for example, by a special geometric design (e.g., a sheet-metal cover) or optical design of the passage opening (for example, as a plate of milk glass), or by a special arrangement of the light source, or by a suitable surface roughness of, for example, the boundaries of the passage opening, which diffusely scatters the light of the light source provided for external illumination. Techniques for designing diffusely scattering surfaces or diffusely scattering light passage openings are generally known to those skilled in the art.

The optical passage may, in principle, be disposed anywhere on the microscope or the stand. Preferably, the passage opening is disposed on the microscope body or on a parallelogram linkage support.

The at least one optical passage is preferably configured as a gap or slot on the microscope body or the stand. Preferably, provision is made for a plurality of narrow slots or gaps.

Preferably, at least one of the passage openings is closed with a transparent cover so as, for example, to prevent even the smallest quantities of dust particles or other types of air pollution particles from entering the microscope or its components. This may advantageously be achieved by designing the cover itself as a diffuser for homogenizing the emerging light. However, it is also possible to dispose a diffuser inside of the microscope body or the stand in the vicinity of the light source.

Light sources 17 are arranged in a row within cavity 16, here, for example, along a central line and such that said row of light sources does not extend into the area of the optical path of the microscope. Inner surfaces 29 of walls 19 and 31 of cavity 16 may be provided with reflectors or reflective coatings.

Figure 6:
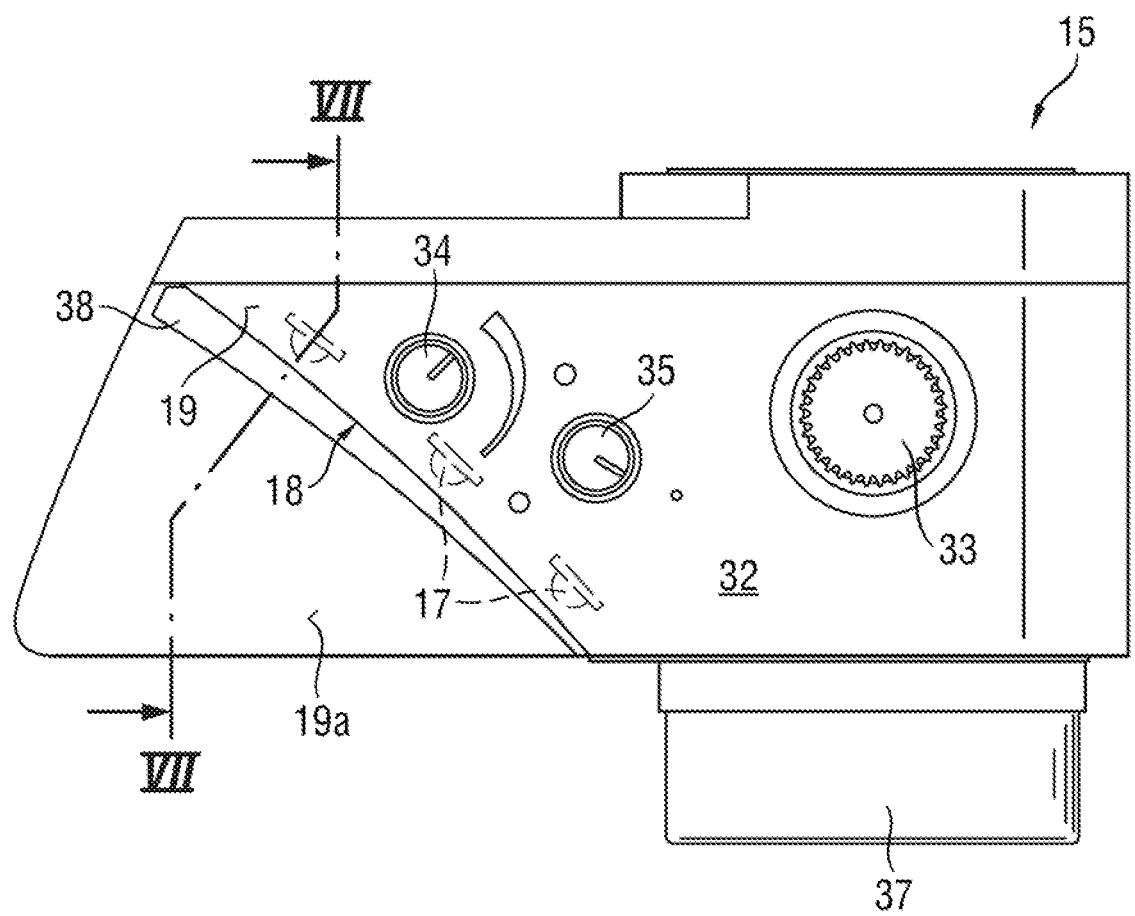
FIG. 6 is a side view of a modified housing body of the dental microscope shown in FIG. 1.

FIG. 6 shows in greater detail the portion of control panel 32 of microscope body 15. In particular, for example, reference numeral 33 denotes the adjustment means of objective 37, numeral 34 designates the control of light sources 17, and numeral 35 denotes the control of room lighting 12. Here, opening 18 for the exit of light is in the form of a longitudinal slot extending obliquely and convexly from top left to bottom right.

Figure 7:
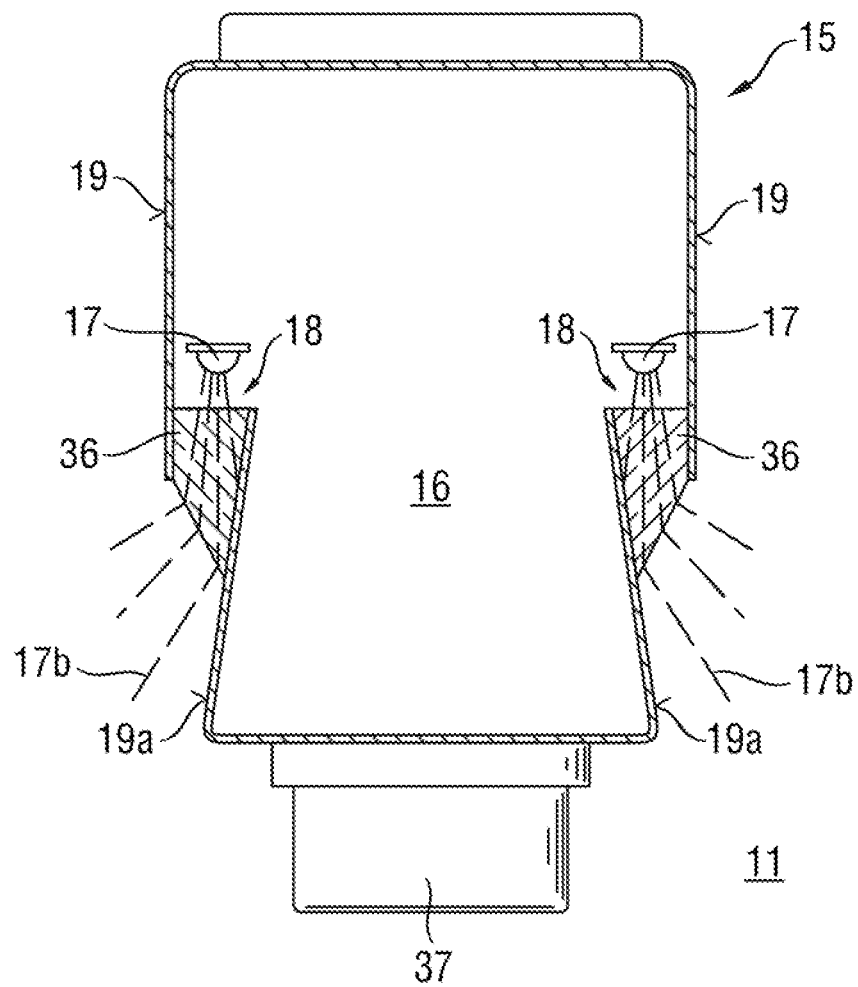
FIG. 7 is a vertical sectional view of the housing body of the dental microscope, taken in the plane of line VII-VII in FIG. 6.

Referring to FIG. 7, transparent light-guiding elements 36 are inserted in passage openings 18 on both sides between walls 19, 19a. These light-guiding elements provide a dust-tight seal on the one hand and, on the other hand, produce diverging light rays 17b, and thus homogenized illumination, because of their diffusing properties.

Figure 8:
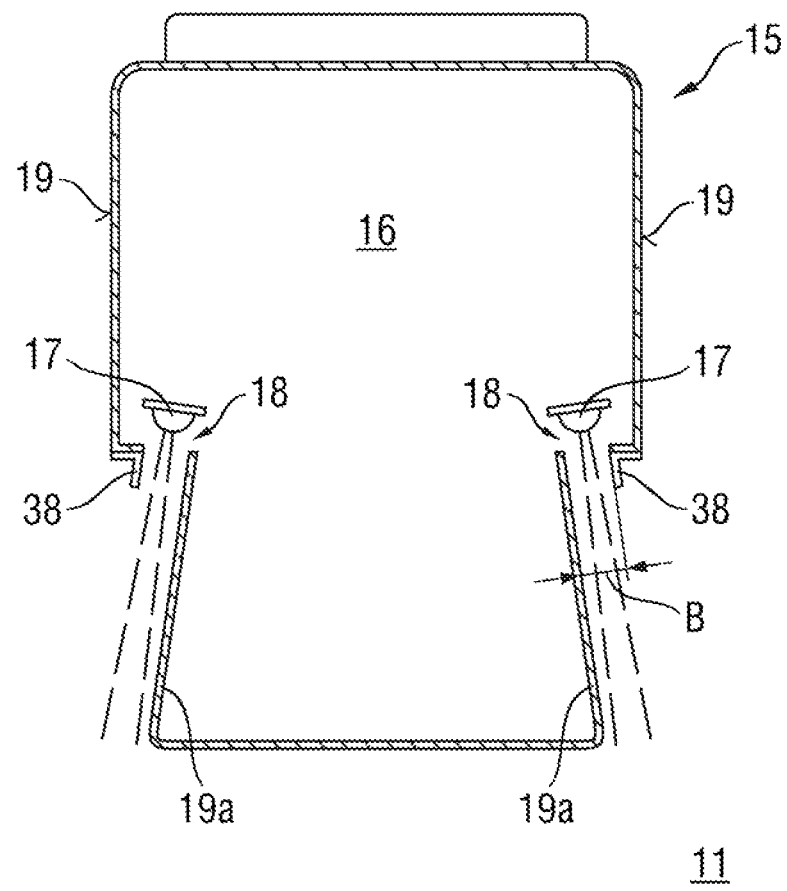
FIG. 8 is a vertical sectional view similar to FIG. 7, showing a further, modified housing body of a dental microscope, in which the light exit openings are provided with light shield sections for adjustment of their width.

As shown in FIGS. 6 and 8, passage openings 18 may be provided with angle sections 38 to provide a means for adjusting the width B of passage openings 18.

FIG. 1 and FIGS. 9 through 12 illustrate the arrangement of light sources 17 for indirect illumination on support arms 6 and 5.

Figure 9:
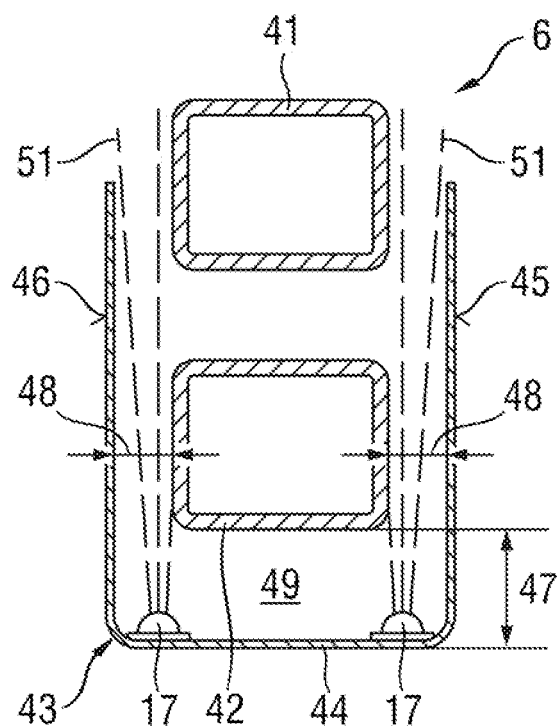
FIG. 9 is a vertical sectional view taken in the plane of line IX-IX in FIG. 1 and showing the illumination arrangement on the stand in the region of the second support arm, which is in the form of a parallelogram support arm.

Referring in particular to FIGS. 1 and 9, support arm 6 is configured as a parallelogram linkage arm which ensures constant vertical guidance during height adjustment of microscope 1. The parallelogram linkage arm is formed by two arm members arranged parallel to one another. The upper arm member is denoted by 41, while the lower arm member is denoted by 42.

A U-shaped covering 43 including a bottom web 44 and two lateral flanges 45 and 46 is mounted to hub 8a (FIG. 1) of joint 8 in such a way that bottom web 44 is located under lower arm member 42 at a distance 47 therefrom.

The resulting clearance 49 accommodates indirect illumination means in the form of light sources 17, which are arranged in such a way that two rows of light sources 17 direct indirect light radiation 51 upwardly through gaps 48 between support arm 6, which is formed by arm members 41 and 42, and lateral flanges 45 and 46, thereby also illuminating the side surfaces of the two arm members 41 and 42.

Figure 10:
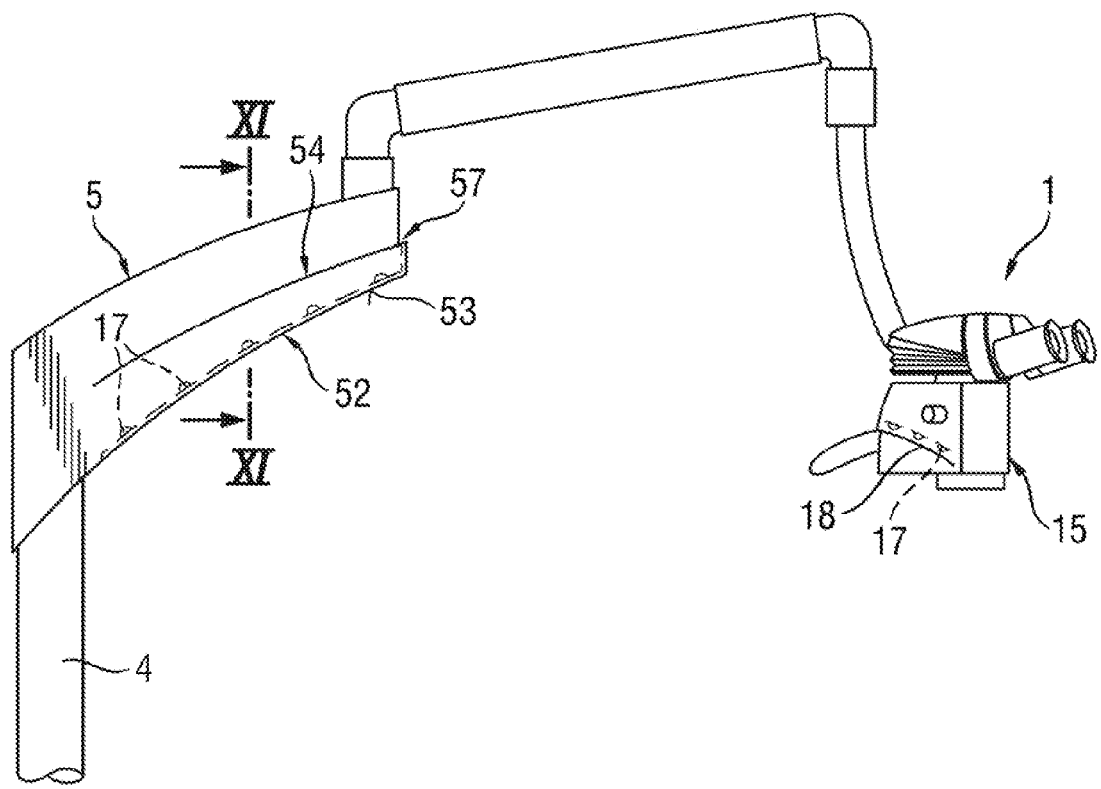
FIG. 10 is a view of a variant of the upper portion of the stand shown in FIG. 1, in which the first support arm, which is pivotally attached to the stand pole, is provided with an indirect illumination system.
Figure 11:
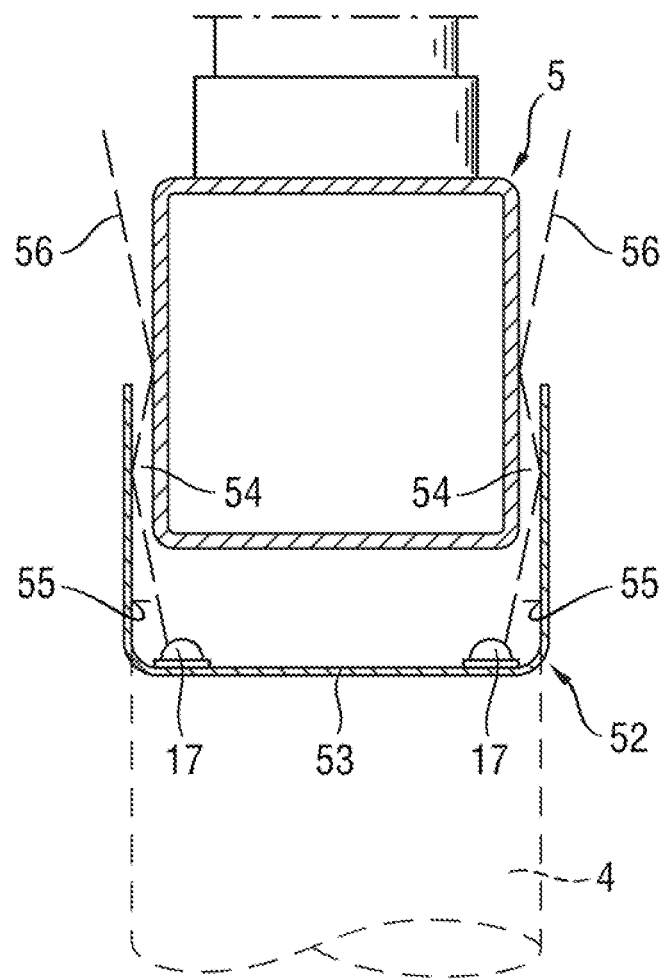
FIG. 11 is a vertical sectional view taken in the plane of line XI-XI in FIG. 10 and showing the indirect illumination system in the form of two rows of light sources arranged along the sides.

The indirect illumination means on first support arm 5 are configured similar to those mentioned above. Referring to FIGS. 10 and 11, first support arm 5 is provided in its lower region with a U-shaped covering 52 which follows the tapering design of support arm 5.

Provided on bottom web 53 are two rows of light sources 17 which emit light upwardly through narrow gaps 54, respectively. Inner surfaces 55 of the covering are reflective, which enables the sets of indirect light rays 56 to travel upwardly and exit to the outside as multiply reflected rays, thereby also illuminating the side walls of first support arm 5. At the right end portion (FIG. 10), covering 52 projects beyond support arm 5, forming a gap 57, so that indirect light can also exit in this region.

Figure 12:
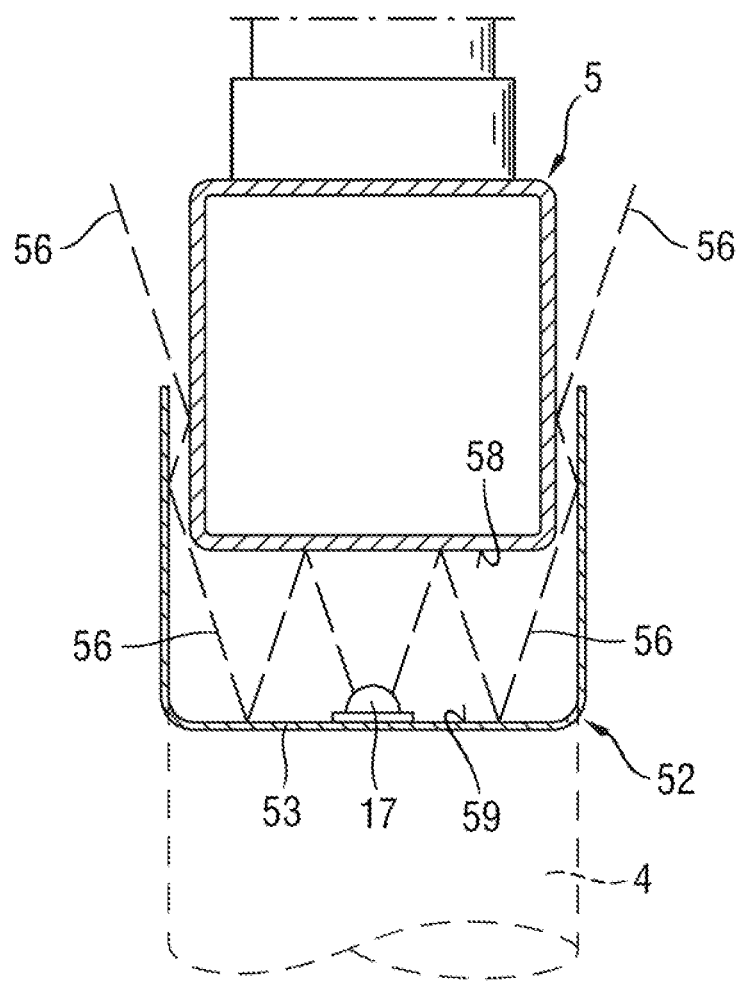
FIG. 12 is a view of a variant of the embodiment of FIG. 11, showing only a single, central row of light sources.

FIG. 12 is a view of a variant of the embodiment of FIG. 11, showing only a single strip of light sources 17 arranged centrally along bottom web 53 of U-shaped covering 52. Here, the sets of light rays 56 are multiply reflected at underside 58 of support arm 5 and inner upper side 59 of bottom web 53 in directions toward two sides.

Figure 13:
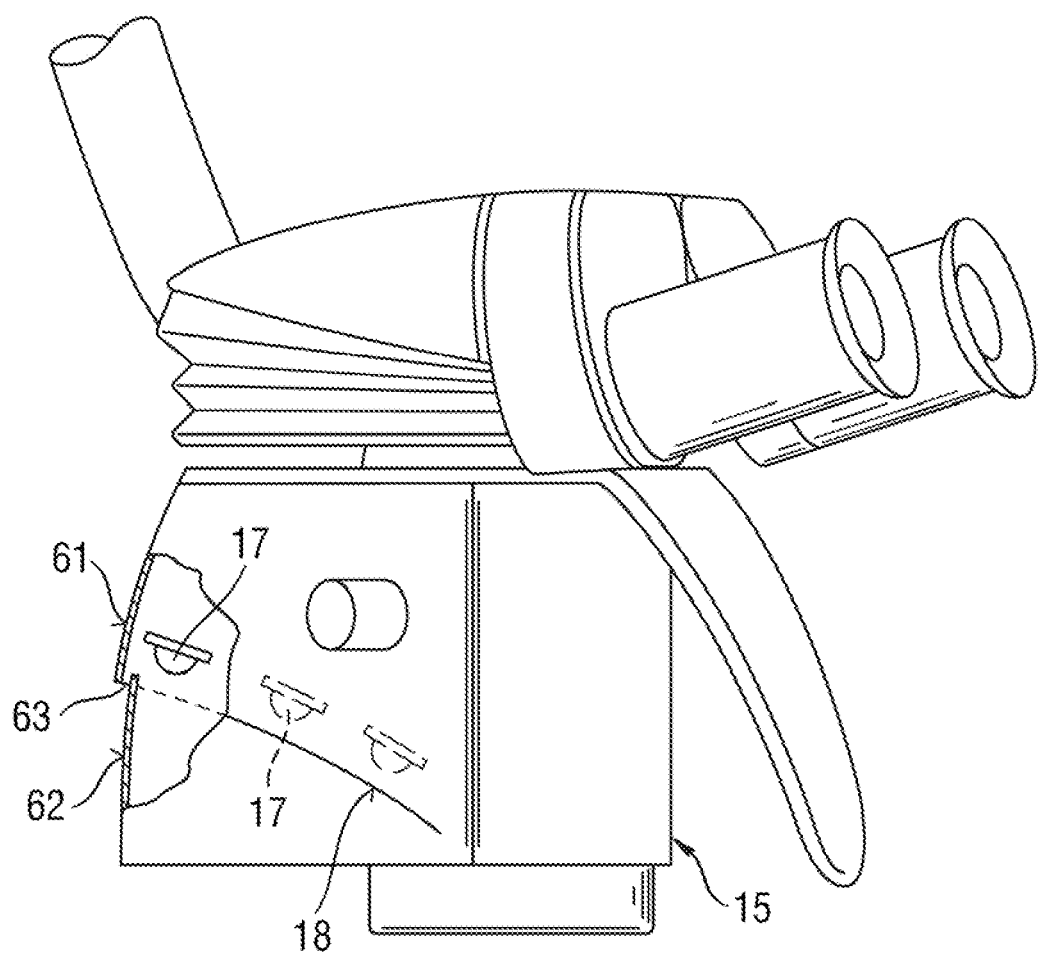
FIG. 13 is a view of the dental microscope corresponding to FIG. 12, partially cut away and in cross section, illustrating the light exit at the rear.

As illustrated in the partially cut away view of FIG. 13, a light exit opening 18 is also provided at the rear of the microscope body 15, opposite the eyepieces mounted on the microscope body 15. In particular, rear walls 61 and 62 are offset from each other, forming and bounding a further slotted opening 63. Thus, the microscope body is provided on three sides with passage openings 18, 63, 18 for indirect light exit.

In addition to the technical advantages mentioned above, the present invention and the described embodiments provide further advantages for a user:

The exterior appearance of a microscope according to the present invention may be adapted to the surrounding space, for example, in a dentist's office. Prior art microscope bodies, stands, and support arms thereof, are known to have either untreated surfaces or surfaces treated with paints or other surface finishes. The use of indirect illumination by light that emerges from the unit through gaps or slots and is emitted indirectly to provide a surface appearance and an exterior appearance that are variable over time and/or variable in color has been unknown.

Unlike conventional microscopes, the visually apparent space requirements of the unit in a doctor's office or an operating room can be influenced by means of the indirect external illumination. The present invention enables the appearance of a microscope, in particular a dental microscope or a surgical microscope, to be adapted to the needs of the user, or to the conditions of the room, by turning the external illumination on/off, by controlling its brightness and/or by selecting the color of its light.

In an environment with high requirements on cleanliness, such as a doctor's or dentist's office, it is preferred to use blue light for the external illumination, because it is known from experience that blue light enhances the impression of hygiene and, in addition, because bacteria avoid blue tones. Blue tones are therefore bacteriophic. Moreover, light having shorter wavelengths down to the UV region has a bactericidal effect and, therefore, allows a microscope equipped in accordance with the present invention to be brought into a bactericidal condition when no people are present. As such, the light can be automatically selected from bacteriophic wavelengths of light when the microscope is out of use.

Accordingly, in addition to the purely technical effects, it is also possible to change the coloring of surfaces without the need to replace components or covers, or apply new paint, which allows microscopes and stands to be dynamically adapted to the requirements of users or facilities.

LIST OF REFERENCE NUMERALS 1 microscope, preferably a dental microscope
2 stand
3 base
4 pole
5 first support arm
6 second support arm
7 third support arm
8 joint
8a hub of 8
9 joint
11 room
12 room lighting (referred to as external room lighting)
13 head portion of 1
14 eyepiece
15 microscope body
16 cavity of 15
17 light sources (LEDs)
17a light rays (direct reflection)
17b light rays (homogenized light)
17c light rays (divergent)
18 passage openings (in the form of slots in 19)
19 walls
19a inclined wall section
21 sensor
22 rotary knob for light control
24 light exit opening
25 transparent ground glass plate (having light-diffusing and homogenizing properties)
26 pocket, recess, retaining receptacle
27 light passage opening
28 cover plate
29 inner surfaces (reflective)
31 wall of 15 (at the top)
32 control panel
33 adjustment means for objective 37
34 control for light source 17
35 control for room lighting 12
36 light-guiding elements (having diffusing properties)
37 objective
38 angle section (for the adjustment of B)
41 upper arm member of 6
42 lower arm member of 6
43 U-shaped covering
44 bottom web of 43
45 lateral flange of 43
46 lateral flange of 43
47 distance 48 gap
49 clearance
51 indirect light radiation
52 covering
53 bottom web
54 gap
55 surface
56 sets of light rays
57 gap
58 underside
59 upper side
61 upper rear wall of 15
62 lower rear wall of 15
63 slotted opening
B width of opening 18 (FIG. 8)
64 electronic control system

What is claimed is:

1. An apparatus comprising:
a microscope including a microscope body;
an object field light source for object field illumination;
a stand on which the microscope is mounted, the stand including a plurality of support arms arranged to support the microscope, the support arms being adjustable for positioning the microscope in a room; and
at least one of the microscope and the stand including a cavity therein and a light-transmitting passage opening from the cavity to the room, and at least one light source located in the cavity, the at least one light source being arranged to emit light outwardly through the associated passage opening into the room;
wherein the associated passage opening is disposed such that the emitted light from the at least one light source indirectly illuminates an exterior surface of the microscope or of the stand apart from the area to be viewed through the microscope, and wherein the passage opening is defined by a gap or a slot on the microscope body or on the stand.

2. The apparatus according to claim 1, wherein a respective cavity, light-transmitting passage opening, and at least one light source are provided on the microscope and the stand.

3. The apparatus as recited in claim 2, wherein the plurality of support arms of the stand comprise a parallelogram linkage and a plurality of light sources disposed in the cavity.

4. The apparatus as recited in claim 2, wherein each of the associated passage openings has a surface configuration or a cover preventing light from being emitted directly into the room and producing diffuse light emission into the room.

5. The apparatus as recited in claim 1, wherein the at least one light source is adjustable in at least one of output intensity and color of the emitted light.

6. The apparatus as recited in claim 5, wherein the at least one light source is automatically adjustable in at least one of output intensity and color of the emitted light according to a timing sequence.

7. The apparatus as recited in claim 5, wherein the at least one light source comprises a plurality of light sources.

8. The apparatus as recited in claim 7, wherein a plurality of passage openings are provided through which light emitted by the plurality of light sources thereof passes into the room.

9. The apparatus as recited in claim 7, wherein at least one of the output intensity and the color of the emitted light is adjusted automatically, the automatically adjustable light intensity or color being assigned to a specified operating condition or operating mode indication from a group of different operating conditions or operating mode indications of the microscope or the stand, said group consisting of the following operating mode indications: a magnification setting of the microscope, a zoom setting of the microscope, diopter settings of a pair of eyepieces of the microscope, a balancing condition of the stand or the microscope, and an operational readiness of an accessory.

10. The apparatus as recited in claim 9, wherein at least one of the light output intensity and the light color corresponds to a magnification setting of the microscope.

11. The apparatus as recited in claim 9, wherein at least one of the light output intensity and the light color corresponds to a selected diopter setting of an eyepiece of the microscope.

12. The apparatus as recited in claim 9, wherein the light color is automatically selected from a range of bactericidal or bacteriophic wavelengths of light when the microscope is out of use.

13. The apparatus as recited in claim 9, wherein the pair of eyepieces of the microscope are adjustable to different diopter settings, and two different light colors are emitted onto two different exterior sides of the microscope body or the stand.

14. The apparatus as recited in claim 9, wherein a plurality of operating conditions or operating mode indications of the microscope can be displayed simultaneously by one or more different light colors.

15. The apparatus as recited in claim 9, further comprising a sensor arranged to measure at least one of a color temperature and a light intensity of an external room lighting, wherein the sensor is connected to an electronic control system associated with the plurality of light sources for adapting at least one of the light color and the light intensity of the light emitted by the plurality of light sources in response to a signal from the sensor.

16. The apparatus as recited in claim 15, wherein the light color of the light emitted by the plurality of light sources is adapted to be complementary to the external room lighting.

17. The apparatus as recited in claim 1, wherein the associated passage opening is disposed such that the light emitted into the room indirectly illuminates the room in which the microscope is located.

18. The apparatus as recited in claim 1, wherein the microscope is a surgical microscope.

19. The apparatus as recited in claim 1, wherein the microscope is a dental microscope.

20. The apparatus as recited in claim 1, wherein the associated passage opening has a surface configuration or a cover preventing light from being emitted directly into the room and producing diffuse light emission into the room.

21. The apparatus as recited in claim 1, wherein the associated passage opening has a transparent cover.

22. The apparatus as recited in claim 21, wherein the transparent cover is a diffuser for homogenizing the emitted light.

23. The apparatus as recited in claim 1, wherein the at least one light source is selected from a group consisting of an LED, an OLED, a laser diode, and a nanotube light source.

24. The apparatus as recited in claim 1, wherein the microscope includes a pair of eyepieces mounted at a front of the microscope body and the microscope body includes a rear opposite the front, and the passage opening is defined by a slot on the rear of the microscope body.

25. The apparatus as recited in claim 1, wherein one of the plurality of support arms has a front end, and the passage opening is defined by a gap at the front end of the one support arm.

26. The apparatus as recited in claim 1, wherein the light-transmitting passage opening faces upward.

27. The apparatus as recited in claim 1, wherein the light-transmitting passage opening faces downward.

28. A stand for supporting a microscope, the stand comprising:
- a plurality of support arms, the support arms being adjustable for positioning a microscope in a room, at least one of the support arms having a cavity therein, a light-transmitting passage opening from the cavity to the room, and at least one light source located in the cavity, the at least one light source being arranged to emit light outwardly through the associated passage opening into the room;
- an object field light source for object field illumination;
- wherein the associated passage opening is disposed such that the emitted light from the at least one light source indirectly illuminates an exterior surface of the stand apart from the area to be viewed through the microscope, and wherein the passage opening is defined by a gap or a slot on the stand.

* * * * *